(12) United States Patent
Forman (10) Patent No.: US 6,537,195 B2
(45) Date of Patent: Mar. 25, 2003

(54) COMBINATION X-RAY RADIATION AND DRUG DELIVERY DEVICES AND METHODS FOR INHIBITING HYPERPLASIA

(75) Inventor: Michael R. Forman, Vadnais Heights, MN (US)

(73) Assignee: Xoft, microTube, Inc., Fremont, CA (US)

( * ) Notice: Subject to any disclaimer, the term of this patent is extended or adjusted under 35 U.S.C. 154(b) by 17 days.

(21) Appl. No.: 09/850,721

(22) Filed: May 7, 2001

(65) Prior Publication Data

US 2002/0165423 A1 Nov. 7, 2002

(51) Int. Cl.$^7$ ................................................. A61N 5/00
(52) U.S. Cl. ............................. 600/3; 604/21; 604/104; 604/96.01
(58) Field of Search ................. 600/3, 5, 7, 1; 604/21, 104, 508–510, 96.01

(56) References Cited

U.S. PATENT DOCUMENTS

| | | |
|---|---|---|
| 3,976,071 A | 8/1976 | Sadek |
| 4,636,195 A | 1/1987 | Wolinsky |
| 4,832,686 A | 5/1989 | Anderson |

(List continued on next page.)

FOREIGN PATENT DOCUMENTS

| | | |
|---|---|---|
| EP | 688580 | 6/1994 |
| EP | 593136 | 3/1997 |
| EP | 860180 | 8/1998 |
| EP | 633041 | 9/1999 |
| EP | 1057500 | * 12/2000 |
| JP | 2000-279524 | * 10/2000 |
| WO | WO 96/13303 | 5/1996 |
| WO | WO 96/14898 | 5/1996 |
| WO | WO 96/23543 | 8/1996 |
| WO | WO 97/07740 | 3/1997 |
| WO | WO 98/36790 | 8/1998 |
| WO | WO 99/51299 | 10/1999 |
| WO | WO 99/55285 | 11/1999 |
| WO | WO 00/00238 | 1/2000 |
| WO | WO 00/47197 | 8/2000 |
| WO | WO 00/70645 | 11/2000 |
| WO | WO 01/93778 A1 | 12/2001 |

OTHER PUBLICATIONS

Choy, "Taxanes in combined–modality therapy for solid tumors" *Oncology* (1999) 13(10 Suppl. 5):23–38 (abstract) [retrieved on Apr. 5, 2000]. Retrieved from: PMID: 10550824 UI: 20018487.

De Palo et al., "Concurrent radiotherapy and taxol as radiosensitizer in locally advanced or recurrent carcinoma of the uterine cervix. A pilot study" [online abstract], [retrieved on Apr. 13, 2000]. Retrieved from Internet. <URL: http://208.240.92.166/prof/me/html/98abstracts/gync/m$_{13}$1404.htm>1 page total.

Enzinger et al., "Phase I/II neoadjuvant concurrent 96 hour taxol, cisplatin, and radiation therapy: Promising toxicity profile and response in localized esophageal cancer" [online abstract]. [retrieved on Mar. 19, 2000]Retrieved from Internet. <URL: http://www.asco.org/prof/me/htmI/99 abracts/gic/m$_{13}$1038.htm> 1 page total.

(List continued on next page.)

*Primary Examiner*—John A. Jeffery
(74) *Attorney, Agent, or Firm*—Townsend Townsend & Crew LLP; Nena Bains, Esq.

(57) ABSTRACT

The present invention provides improved devices, methods, and kits for inhibiting restenosis and hyperplasia after intravascular intervention. In particular, the present invention provides controlled drug delivery in combination with x-ray radiation delivery to selected locations within a patient's vasculature to reduce and/or inhibit restenosis and hyperplasia rates with increased efficacy. In one embodiment, the combination radiation and agent delivery catheter for inhibiting hyperplasia comprises a catheter body having a proximal end and distal end, an x-ray tube coupleable to the catheter body for applying a radiation dose to a body lumen, and a porous material, matrix, membrane, barrier, coating, infusion lumen, stent, graft, or reservoir for releasing an agent to the body lumen.

42 Claims, 7 Drawing Sheets

U.S. PATENT DOCUMENTS

| | | | |
|---|---|---|---|
| 4,883,666 A | 11/1989 | Sabel et al. | |
| 4,897,268 A | 1/1990 | Tice et al. | |
| 5,059,166 A | 10/1991 | Fischell et al. | |
| 5,061,267 A | 10/1991 | Zeiher | |
| 5,090,043 A | 2/1992 | Parker et al. | |
| 5,163,952 A | 11/1992 | Froix | |
| 5,199,939 A | 4/1993 | Dake et al. | |
| 5,213,561 A | 5/1993 | Weinstein et al. | |
| RE34,421 E | 10/1993 | Parker et al. | |
| 5,256,141 A | 10/1993 | Gencheff et al. | |
| 5,286,254 A | 2/1994 | Shapland et al. | |
| 5,302,168 A | 4/1994 | Hess | |
| 5,318,531 A | 6/1994 | Leone | |
| 5,342,348 A | 8/1994 | Kaplan | |
| 5,354,257 A | 10/1994 | Roubin et al. | |
| 5,411,466 A | 5/1995 | Hess | |
| 5,411,550 A | 5/1995 | Herweck et al. | |
| 5,419,760 A | 5/1995 | Narciso, Jr. | |
| 5,464,450 A | 11/1995 | Buscemi et al. | |
| 5,484,384 A | 1/1996 | Fearnot | |
| 5,484,584 A | 1/1996 | Wallace et al. | |
| 5,498,227 A | 3/1996 | Mawad | |
| 5,500,013 A | 3/1996 | Buscemi et al. | |
| 5,503,613 A | 4/1996 | Weinberger | |
| 5,505,613 A | 4/1996 | Krummenacher | |
| 5,540,659 A | 7/1996 | Teirstein | |
| 5,543,158 A | 8/1996 | Gref et al. | |
| 5,545,208 A | 8/1996 | Wolff et al. | |
| 5,551,954 A | 9/1996 | Buscemi et al. | |
| 5,566,221 A * | 10/1996 | Smith et al. | 378/145 |
| 5,569,198 A | 10/1996 | Racchini | |
| 5,591,227 A | 1/1997 | Dinh et al. | |
| 5,609,629 A | 3/1997 | Fearnot et al. | |
| 5,616,114 A | 4/1997 | Thornton et al. | |
| 5,618,266 A | 4/1997 | Liprie | |
| 5,624,372 A | 4/1997 | Liprie | |
| 5,637,113 A | 6/1997 | Tartaglia et al. | |
| 5,643,171 A | 7/1997 | Bradshaw et al. | |
| 5,649,977 A | 7/1997 | Campbell | |
| 5,653,736 A | 8/1997 | Glastra | |
| 5,656,297 A | 8/1997 | Bernstein et al. | |
| 5,679,400 A | 10/1997 | Tuch | |
| 5,681,558 A | 10/1997 | Johns et al. | |
| 5,700,286 A | 12/1997 | Tartaglia et al. | |
| 5,704,908 A * | 1/1998 | Hofmann et al. | 604/21 |
| 5,735,811 A | 4/1998 | Brisken | |
| 5,769,883 A | 6/1998 | Buscemi et al. | |
| 5,772,642 A * | 6/1998 | Ciamacco, Jr. et al. | 604/280 |
| 5,800,392 A * | 9/1998 | Racchini | 604/96.01 |
| 5,837,008 A | 11/1998 | Berg et al. | |
| 5,843,172 A | 12/1998 | Yan | |
| 5,851,231 A | 12/1998 | Wolff et al. | |
| 5,863,285 A | 1/1999 | Coletti | |
| 5,876,452 A | 3/1999 | Athanasiou et al. | |
| 5,891,108 A | 4/1999 | Leone et al. | |
| 5,893,840 A | 4/1999 | Hull et al. | |
| 5,947,889 A * | 9/1999 | Hehrlein | 600/3 |
| 5,951,458 A | 9/1999 | Hastings et al. | |
| 5,951,586 A | 9/1999 | Berg et al. | |
| 5,968,092 A | 10/1999 | Buscemi et al. | |
| 5,971,909 A | 10/1999 | Bradshaw et al. | |
| 5,972,027 A | 10/1999 | Johnson | |
| 5,980,551 A | 11/1999 | Summers et al. | |
| 5,980,566 A | 11/1999 | Alt et al. | |
| 5,985,307 A * | 11/1999 | Hanson et al. | 424/423 |
| 5,993,374 A | 11/1999 | Kick | |
| 5,997,468 A | 12/1999 | Wolff et al. | |
| 6,063,101 A | 5/2000 | Jacobsen et al. | |
| 6,069,938 A | 5/2000 | Chornenky et al. | |
| 6,071,305 A | 6/2000 | Brown et al. | |
| 6,072,038 A | 6/2000 | Sessler et al. | |
| 6,095,966 A | 8/2000 | Chornenky et al. | |
| 6,099,561 A | 8/2000 | Alt | |
| 6,108,402 A | 8/2000 | Chornenky | |
| 6,149,574 A * | 11/2000 | Trauthen et al. | 600/3 |
| 6,183,409 B1 | 2/2001 | Armini | |
| 6,210,393 B1 * | 4/2001 | Brisken | 604/508 |
| 6,390,967 B1 * | 5/2002 | Froman et al. | 600/3 |
| 6,398,709 B1 | 6/2002 | Ehr et al. | |
| 6,400,796 B1 | 6/2002 | Munro, III et al. | |

OTHER PUBLICATIONS

Kessler et al., "Effects of human interferons and 60 cobalt radiation on canine and feline tumor cells–preclinical studies" [online], [retrieved on May 18, 2000]. Retrieved from Internet. <URL: http://130.14.32.42/cgi–bin/VERSION$_{13}$A/IGM–cient?15504+records+161> Source: *Zentralbl. Veterinarmed. A.* (1996) 43(10:599–609. 1 page total.

Lederman, "Combining chemotherapy and radiation" [online], [retrieved on Apr. 5, 2000]. Retrieved from Internet. <URL: http://www.siuh.edu/radoncology/charticle3.html> 2 pages total.

Wright, "Molecular radiosensitizers target proliferation and apoptosis pathways in tumour cells" *Oncolog* (2000) 45(11):4 pages total.

Schmidberger et al., "The combine effect of interferon beta and radiation on five human tumor cell lines and embryonal lung fibroblasts" [online abstract], Retrieved from Internet. <URL: http:// 130.14.32.42/cgi–bin/VERSION$_{13}$A/IGM–cient?15504+records+61> Source: *Int. Radiat. Oncol. Biol. Phys.* (1999) 43(2):405–412. 1 page total.

SCVIR Meeting, San Francisco, CA, Mar. 02, 1998, "Taxol may help prevent bloods vessels from re–clogging" [online], [retrie on Mar. 19, 2000]. Retrieved from Internet. <URL: plsgroup.com/dg/5e37a.htm> 3 pages total.

* cited by examiner

COMBINATION X-RAY RADIATION AND DRUG DELIVERY DEVICES AND METHODS FOR INHIBITING HYPERPLASIA

BACKGROUND OF THE INVENTION

1. Field of Invention

The present invention relates generally to medical devices and methods for inhibiting restenosis in a blood vessel after an initial treatment for opening a stenotic region in a blood vessel. More particularly, the present invention relates to combination x-ray radiation and drug delivery devices for inhibiting hyperplasia following balloon angioplasty and other interventional treatments.

A number of percutaneous intravascular procedures have been developed for treating stenotic atherosclerotic regions of a patient's vasculature to restore adequate blood flow. The most successful of these treatments is percutaneous transluminal angioplasty (PTA). In PTA, a catheter, having an expansible distal end usually in the form of an inflatable balloon, is positioned in the blood vessel at the stenotic site. The expansible end is expanded to dilate the vessel to restore adequate blood flow beyond the diseased region. Other procedures for opening stenotic regions include directional atherectomy, rotational atherectomy, laser angioplasty, stenting, and the like. While these procedures have gained wide acceptance (either alone or in combination, particularly PTA in combination with stenting), they continue to suffer from significant disadvantages. A particularly common disadvantage with PTA and other known procedures for opening stenotic regions is the frequent occurrence of restenosis.

Restenosis refers to the re-narrowing of an artery after an initially successful angioplasty. Restenosis afflicts approximately up to 50% of all angioplasty patients and is the result of injury to the blood vessel wall during the lumen opening angioplasty procedure. In some patients, the injury initiates a repair response that is characterized by smooth muscle cell proliferation referred to as "hyperplasia" in the region traumatized by the angioplasty. This proliferation of smooth muscle cells re-narrows the lumen that was opened by the angioplasty within a few weeks to a few months, thereby necessitating a repeat PTA or other procedure to alleviate the restenosis so that blood perfusion may be restored.

A number of strategies have been proposed to treat hyperplasia and reduce restenosis. Previously proposed strategies include prolonged balloon inflation during angioplasty, treatment of the blood vessel with a heated balloon, stenting of the region, use of radiotherapy to treat in-stent restenosis, the administration of therapeutic drugs following angioplasty, and other procedures. While these proposals have enjoyed varying levels of success, no one of these procedures is proven to be entirely successful in completely avoiding all occurrences of restenosis and hyperplasia.

As an alternative to the above mentioned therapies, the combination of radioisotope radiation and drug therapy following PTA for the inhibition of hyperplasia has also been proposed. Drug therapy infuses or releases a drug through a catheter or from a stent, while intravascular radiotherapy may configure catheters, guidewires, and stents to position a solid radioisotopic source (such as a wire, strip, pellet, seed, bead, or the like). While combination delivery of therapeutic agents with radioisotopic sources holds promise, there may be circumstances where certain agents and sources would be particularly advantageous.

For these reasons, it would be desirable to provide improved devices and methods for inhibiting restenosis and hyperplasia following angioplasty and other interventional treatments. In particular, it would be desirable to provide improved devices, methods, and kits for drug delivery in combination with x-ray radiation delivery to a blood vessel to reduce and/or inhibit restenosis and hyperplasia rates with increased efficacy. It would further be desirable to provide such devices and methods which significantly reduce dose concentrations of drugs and/or radiation within the vessel wall while delivering sufficiently uniform radiation dosages and promoting endothelialization of the vessel wall. At least some of these objectives will be met by the devices and methods of the present invention described hereinafter.

2. Description of Background Art

Full descriptions of exemplary x-ray sources for use in the present invention are described in co-pending U.S. patent application Ser. No. 09/299,304, assigned to the assignee herein, and U.S. Pat. No. 6,095,966, licensed to the assignee herein. Devices and methods for exposing intravascular and other treatment locations to radioisotopic materials in combination with therapeutic drugs are described in the following: U.S. Pat. Nos. 6,149,574; 5,993,374; 5,951,458; and International Publication Nos. WO 00/47197; WO 00/00238; WO 99/55285; WO 99/51299; WO 98/36790; and WO 96/23543. The use of texaphyrins for radiation sensitization is described in U.S. Pat. No. 6,072,038. Devices and methods for exposing intravascular locations to radioactive materials are described in the following: U.S. Pat. Nos. 6,069,938; 5,971,909; 5,653,736; 5,643,171; 5,624,372; 5,618,266; 5,616,114; 5,540,659; 5,505,613; 5,503,613; 5,498,227; 5,484,384; 5,411,466; 5,354,257; 5,302,168; 5,256,141; 5,213,561; 5,199,939; 5,061,267; and 5,059,166, European applications 860 180; 688 580; 633 041; and 593 136, and International Publications WO 97/07740; WO 96/14898; and WO 96/13303. Drug delivery within the vasculature is described in U.S. Pat. Nos. 6,099, 561; 6,071,305; 6,063,101; 5,997,468; 5,980,551; 5,980, 566; 5,972,027; 5,968,092; 5,951,586; 5,893,840; 5,891, 108; 5,851,231; 5,843,172; 5,837,008; 5,769,883; 5,735, 811; 5,700,286; 5,681,558; 5,679,400; 5,649,977; 5,637, 113; 5,609,629; 5,591,227; 5,551,954; 5,545,208; 5,500, 013; 5,464,450; 5,419,760; 5,411,550; 5,342,348; 5,286, 254; and 5,163,952. Biodegradable materials are described in U.S. Pat. Nos. 5,876,452; 5,656,297; 5,543,158; 5,484, 584; 4,897,268; 4,883,666; 4,832,686; and 3,976,071.

The disclosure of this application is related to the disclosures of the following applications being filed on the same day: Ser. No. 09/851,372 and Ser. No. 09/850,728.

The full disclosures of each of the above references are incorporated herein by reference.

SUMMARY OF THE INVENTION

The present invention provides improved devices, methods, and kits for inhibiting restenosis and hyperplasia after intravascular intervention. In particular, the present invention provides controlled drug delivery in combination with x-ray radiation delivery to selected locations within a patient's vasculature to reduce and/or inhibit restenosis and hyperplasia rates with increased efficacy. The methods and apparatus of the present invention can significantly reduce dose concentrations of drugs and/or radiation within the vessel wall while delivering sufficiently uniform radiation dosages and promoting endothelialization of the vessel wall.

The term "intravascular intervention" includes a variety of corrective procedures that may be performed to at least partially resolve a stenotic condition. Usually, the corrective procedure will comprise balloon angioplasty. The corrective procedure could also comprise atherectomy, rotational atherectomy, laser angioplasty, stenting, or the like, where the lumen of the treated blood vessel is enlarged to at least partially alleviate a stenotic condition which existed prior to the treatment. The corrective procedure could also involve coronary artery bypass, vascular graft implantation, endarterectomy, or the like.

By "controlled" drug delivery, it is meant that a predetermined amount of a drug or agent is released or delivered at a predetermined rate to a blood vessel. Typically, such controlled delivery maintains a steady-state concentration of the drug in a vascular environment within a desired therapeutic range of time, e.g. hours, days, weeks, or in some cases months.

In a first aspect of the present invention, a combination radiation and agent delivery catheter for inhibiting hyperplasia generally comprises a catheter body having a proximal end and distal end, an x-ray tube coupleable to the catheter body for applying a radiation dose to a body lumen, and means coupleable to the catheter body for releasing an agent to the body lumen. The body lumen may be any blood vessel in the patient's vasculature, including veins, arteries, aorta, and particularly including peripheral and coronary arteries.

The means may comprise a source of at least one agent selected from the group consisting of radiosensitizer, immunomodulator, cytotoxic agent, cytostatic agent, antirestenotic agent, and anti-inflammatory agent. The agent may also be a prodrug (e.g., precursor substances that are converted into an active form in the body) of any of the above described agents. Preferably, the means comprises a source of at least one radiosensitizer or immunomodulator. Radiosensitizers may be selected from the group consisting of taxol, misonidazole, metronidazole, etanidazole, 5-fluorouracil, texaphyrin, C225 (an anti-EGFR monoclonal antibody), and cyclooxygenase-2 inhibitor. Immunomodulators may be selected from the group consisting of rapamycin, beta interferon, alpha interferon, methotraxate, cyclosporine, six-mercaptopurine, and cimetidine. More preferably, the means comprises a source of rapamycin, beta interferon, and/or taxol, incorporated in a solution with polyoxyethylated castor oil and dehydrated alcohol. The agent may also be attached or encapsulated in a lipid or surfactant carrier.

The combination of drugs and x-ray radiation therapy reduces and/or inhibits restenosis and hyperplasia rates with increased efficiency. In some instances, at least, it will be expected that the x-ray dosage will provide an immediate inhibition of cell proliferation while the drugs, which may be released over relatively long periods of time, e.g. days, weeks, or in some cases months, will provide prolonged inhibition. In particular, it will be appreciated that many of the above described agents may perform a variety of functions, including minimizing proliferative/restenotic activity, promoting endothelialization of the vessel wall, which is needed for healing, providing synergistic enhancement to radiation effects, and the like. Furthermore, a combined balance of both therapies allows for reduced dosages/concentrations of radiation and/or drugs in the body lumen, as compared to relying on a single therapy with an increased dosage which may not be as effective. Moreover, an x-ray tube provides many advantages as it permits convenient dosing where the source may be easily turned on and off, eliminates the need to prepare, handle, and dispose of radioisotopes, and the like.

It will be appreciated that there are a number of means available for releasing any of the above described agents. Conventional intravascular delivery devices typically comprise a source of the agent, that may be external or internal to the device, and means for controlled drug release to the body lumen. Such means may comprise a porous material which contains the agent, wherein the agent may elute out at a controlled rate from the pores. Such means may alternatively comprise a matrix, membrane, barrier, or coating which includes the agent. Usually, such a matrix comprises a rate controlling material, wherein the rate controlling material controls the rate at which the agent is released from the matrix. Such means may further comprise an infusion lumen for agent release or a drug eluting stent or graft. Still further, such means may comprise a reservoir containing the agent and a cover over the reservoir. Typically, the cover comprises a matrix, membrane, or barrier which in turn controls the rate at which the agent is released from the reservoir.

In one embodiment, the means for releasing the agent may comprise at least one microporous balloon on the catheter body. It is presently preferred that such a one balloon embodiment be employed in the coronary arteries as these vessels are relatively limited in size. The microporous balloon is usually inflated with any of the above described agents and the agent is released at a controlled rate from the microporous balloon by elution from pores. The microporous balloon is preferably elastic and made from nylon, Pebax, polyurethane, or like materials.

In another embodiment, the means for releasing the agent may comprise a matrix, membrane, barrier, or coating formed over at least a portion of at least one balloon on the catheter body. The agent may be disposed in the matrix or on a surface of the balloon beneath the matrix. The matrix will typically comprise a rate controlling material, wherein the rate controlling material controls the rate at which the agent is released from or through the matrix. The rate controlling material may comprise degradable, partially degradable, nondegradable polymer, synthetic, or natural material. The matrix may degrade by bulk degradation, in which the matrix degrades throughout, or preferably by surface degradation, in which a surface of the matrix degrades over time while maintaining bulk integrity, to allow release of the agent. Alternatively, a nondegradable matrix may release the agent by diffusion through the matrix. Optionally, the rate controlling material may be porous so as to allow elution of the agent from pores.

The x-ray tube may be positionable within any of the above described balloons. Typically, the x-ray tube is translatable along an axial line through a center of the balloon. Any of the above described balloons may further comprise perfusion threading on an outer surface to allow for blood perfusion. Such threading may form a spiral, helical, or angled pattern on the balloon surface. The catheter of the present invention may alternatively be equipped with a perfusion lumen/port to permit blood flow past the balloon when inflated.

In a second aspect of the present invention, a combined radiation and agent delivery catheter for inhibiting hyperplasia generally comprises a catheter body having an infusion lumen for releasing an agent, a pair of axially spaced apart balloons on the catheter body, and an x-ray tube. The x-ray tube applies a radiation dose between the axially spaced apart balloons while the infusion lumen releases the agent therein. It is presently preferred that such a two balloon catheter embodiment be employed in the peripheral arteries as such a structure may help center and correctly position the x-ray source in the peripheral vessels, provide a pocket for drug delivery, and aid in uniform radiation dosimetry, as described in greater detail in copending U.S. patent application Ser. No. 09/653,444, assigned the assignee herein, the full disclosure of which is incorporated herein by reference.

In a third aspect of the present invention, a combined radiation and agent delivery device for inhibiting hyperplasia generally comprises a catheter body, an x-ray tube coupleable to the catheter body, a stent which is releasable from the catheter body, and a source of an agent on the stent. The x-ray tube may be positionable within the catheter body to deliver a radiation dose to a vascular region where the stent have been released while the stent releases the agent after the stent has been implanted in a body lumen. The stent may release the agent in a variety of conventional forms. For example, the stent may incorporate a rate controlling matrix, membrane, barrier, or coating to provide controlled release of the agent from the matrix. The agent will typically be disposed on or within the stent or within the matrix. Alternatively, the stent may incorporate a porous material which contains the agent, wherein the agent may elute out at a controlled rate from the porous material. Still further, the stent may incorporate a reservoir containing the agent and a cover over the reservoir. Typically, the cover comprises a matrix, membrane, or barrier which in turn controls the rate at which the agent is released from the reservoir.

In a fourth aspect of the present invention, methods for inhibiting hyperplasia are provided. One method includes releasing an anti-hyperplasia agent at a target region within the body lumen and directing x-ray radiation at the target region, wherein the agent and the x-ray radiation combine to inhibit hyperplasia. The "target region" will be a length within a blood vessel which is at risk of hyperplasia, typically as a result of the initial intravascular intervention(s). The method may further comprise inflating a balloon at the target region, wherein the agent is released from the balloon. The balloon may be inflated with the agent so that the agent is released from an interior of the balloon through pores or the agent may be released from a surface of the balloon through a rate controlling matrix. The method may optionally comprise isolating the target region, wherein the agent is released into the isolated region. The isolating may comprises inflating a pair of axially spaced apart balloons or expanding a pair of axially spaced apart mechanical barriers. Typically, the x-ray source is positioned within the balloon or the isolated target region. Positioning of the x-ray tube generally comprises energizing the x-ray tube and translating the x-ray tube to traverse the target region. A total radiation dose in a range from about 4 Gy to 24 Gy, preferably from 14 Gy to 20 Gy is applied to the target region. The total amount of agent released will typically depend on the specific agent being delivered. The x-ray radiation dose and agent release may additionally be carried out simultaneously or sequentially.

A further method for combination radiation and agent delivery comprises positioning an x-ray tube and a stent at a target region in the body lumen. An x-ray radiation dose is applied to the target region and an agent is released from the stent to the target region.

In a fifth aspect of the present invention, kits comprising a catheter and instructions on how to use the catheter are provided. The kit may also include a source of the agent. The catheter may comprise any of the delivery structures described herein, while the instructions for use will generally recite the steps for performing one or more of the above described methods. The instructions will often be printed, optionally being at least in-part disposed on packaging. The instructions may alternatively comprise a videotape, a CD-ROM or other machine readable code, a graphical representation, or the like showing any of the above described methods.

DESCRIPTION OF THE SPECIFIC EMBODIMENTS

The present invention provides improved devices, methods, and kits for inhibiting restenosis and hyperplasia after intravascular intervention. In particular, the present invention provides controlled drug delivery in combination with x-ray radiation delivery to selected locations within a patient's vasculature to reduce and/or inhibit restenosis and hyperplasia rates with increased efficacy.

Figure 1:
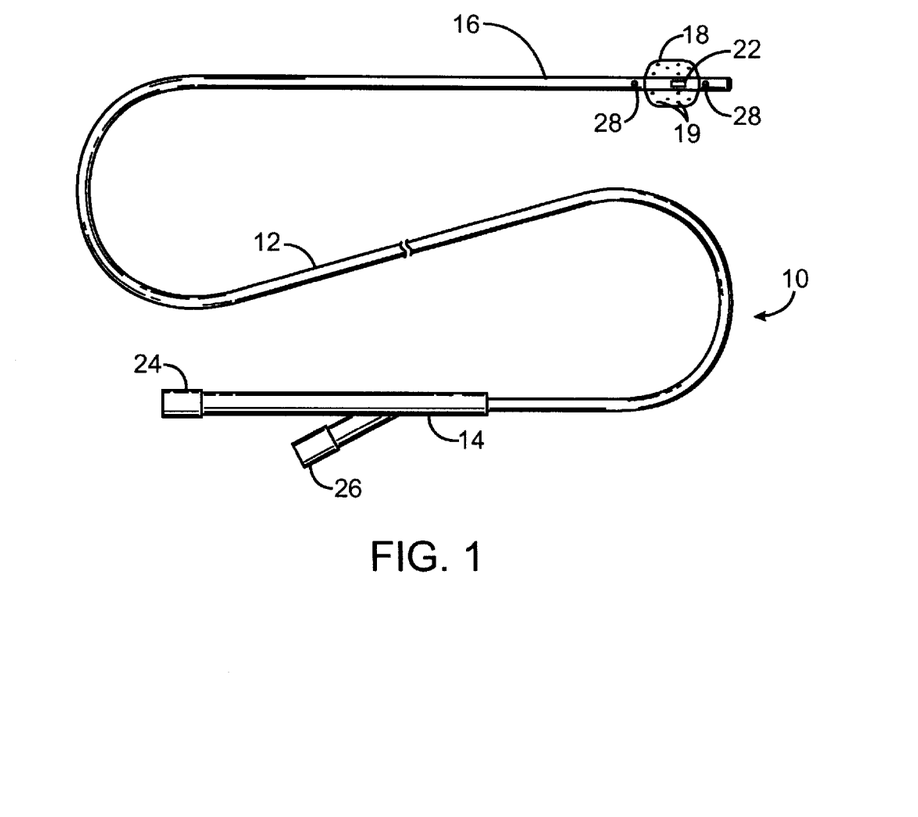
FIG. 1 is a plan view of an apparatus according the present invention.
Figure 2:
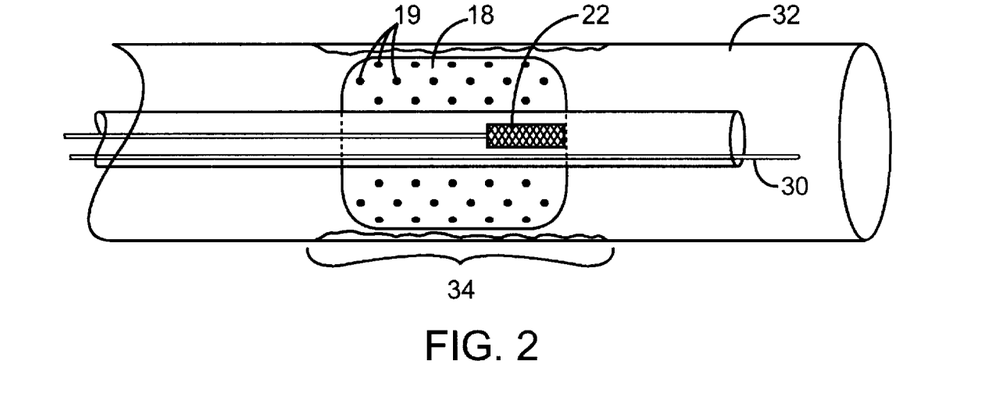
FIG. 2 is a cross sectional view of the apparatus of FIG. 1 within a blood vessel.

FIGS. 1 and 2 illustrate a combination radiation and agent delivery catheter 10 constructed in accordance with the principles of the present invention. The combination radiation and agent delivery catheter 10 comprises a shaft or body 12 having a proximal end 14 and distal end 16, an x-ray tube 22 coupleable to the distal end 16 of the catheter body 12 for applying a radiation dose to a target region 34 in a body lumen 32, and means coupleable to the distal end 16 of the catheter body 12 for releasing an agent 19 to the target region 34. The proximal end 14 of shaft 12 includes a guidewire lumen luer fitting 24 and a balloon luer fitting 26. The guidewire luer fitting 24 is in fluid communication with a guidewire/perfusion lumen that is in turn in fluid communication with perfusion ports 28. Perfusion ports 28 are well known in the art as a means of permitting some blood flow past a balloon 18 that is inflated or otherwise blocking a blood vessel. The balloon luer fitting 26 is in fluid communication with a balloon inflation lumen that is in turn in fluid communication with balloon 18. It will be appreciated that the following depictions are for illustration purposes only and does not necessarily reflect the actual shape, size, or distribution of the delivery catheter 10.

The body lumen 32 may be any blood vessel in the patient's vasculature, including veins, arteries, aorta, and particularly including peripheral and coronary arteries. It will be appreciated that the present invention may also find use in body lumens 32 other than blood vessels. For example, the present invention may be applied to many internal corporeal tissue organs, such as organs, nerves, glands, ducts, and the like.

The radiation source is an x-ray tube 22. The x-ray tube 22 can be isotropic, such as a transmission anode, or non-isotropic, such as an opaque anode. The x-ray will typically operate at an energy in the range from 18 kV to 28 kV. Exemplary x-ray sources 22 are described in co-pending U.S. patent application Ser. No. 09/299,304, assigned to the assignee herein, and U.S. Pat. No. 6,095,966, licensed to the assignee herein. Other suitable x-ray sources are described in U.S. Pat. Nos. 6,134,300 and 5,428,658, and U.S. Pat. No. Reissue 34,421, the full disclosures of which are incorporated herein by reference. The total amount of radiation applied depends in part on the level and amount of vessel injury, as well as the total amount of agent delivered, and will typically be in a range from about 4 Gy to 24 Gy, preferably from 14 Gy to 24 Gy. As described above, an x-ray tube 22 is preferred as it provides many advantages, such as, convenient dosing where the source may be easily turned on and off, eliminates the need to prepare, handle, and dispose of radioisotopes, and the like.

A wide variety of pharmacological agents 19 may be effectively delivered with x-ray radiation in the present invention. Suitable agents 19 include radiosensitizers, immunomodulators, cytotoxic agents, cytostatic agents antirestenotic agents, and anti-inflammatory agents. The agent 19 may also be a prodrug of any of the above described agents. Preferably, the agent is at least one radiosensitizer or immunomodulator. Radiosensitizers may be selected from the group consisting of taxol, misonidazole, metronidazole, etanidazole, 5-fluorouracil, texaphyrin (e.g., Xcytrin™ sold commercially by Pharmacyclics, and RSR13™ sold commercially by Allos Therapeutics), C225, and cyclooxygenase-2 inhibitor. Immunomodulators may be selected from the group consisting of rapamycin, beta interferon, alpha interferon, methotraxate, cyclosporine, six-mercaptopurine, and cimetidine. More preferably, the agent 19 comprises rapamycin, beta interferon, or taxol, alone or in combination with any of the other agents described above. The total amount of agent released depends on the specific agent being delivered as well as on the level and amount of vessel injury and the total amount of radiation applied. For example, rapamycin may be released at levels of 130 micrograms/cm$^3$ or less, while taxol may be released at levels of 130 micrograms/cm$^3$ or less.

The combination of drugs 19 and x-ray radiation 22 reduces and/or inhibits restenosis and hyperplasia rates with increased efficiency. In some instances, at least, it will be expected that the x-ray dosage will provide an immediate inhibition of cell proliferation while the drugs, which may be released over relatively long periods of time, e.g. days, weeks, or in some cases months, will provide prolonged inhibition. In particular, the agents 19 delivered may minimize proliferative/restenotic activity, promote endothelialization of the vessel wall, which is needed for healing, provide synergistic enhancement to radiation effects, and the like. Moreover, combining both therapies allows for reduced dosages/concentrations of both radiation and drugs in the body lumen, as compared to relying on a single therapy with an increased dosage.

Figure 3A:
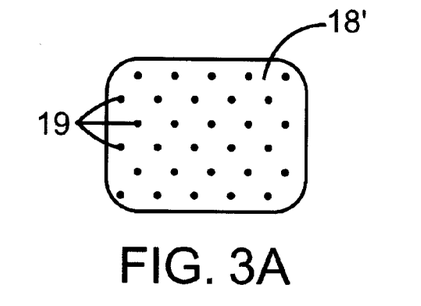
FIGS. 3A–3C illustrate various means for releasing an agent.

Referring now to FIGS. 2 and 3A, the means for releasing the agent may comprise at least one microporous balloon 18 on the catheter body 12. It is presently preferred that such a one balloon embodiment be employed in the coronary arteries. The microporous balloon 18 is usually inflated with any of the above described agents 19 via the balloon luer fitting 26. The agent 19 is then released from the microporous balloon 18 by elution from pores. The microporous balloon 18 is preferably elastic and made from nylon, Pebax, polyurethane, or like materials, and may be an integral extension of the catheter body 12, or attached to the distal end 16 of the catheter body 12 by suitable adhesives, heat welding, or the like. The catheter body 12 may be formed from conventional materials, such as polyethylenes, polyimides, and copolymers and derivatives thereof.

Figure 3B:
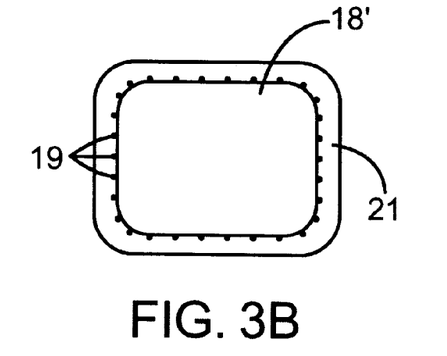
Figure 3C:
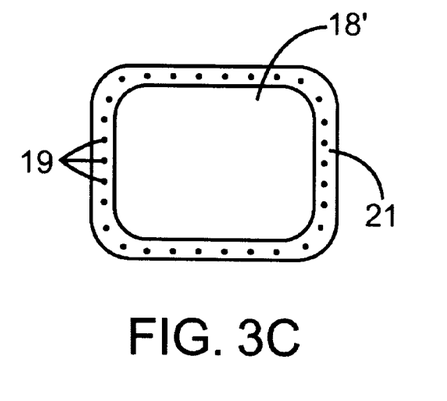

Referring now to FIGS. 3B and 3C, alternative means for releasing the agent may comprise a matrix 21 formed over at least a portion of a balloon 18' on the catheter body 12. The matrix 21 will typically comprise a rate controlling material, wherein the rate controlling material controls the rate at which the agent 19 is released from or through the matrix 21. The agent 19 may be disposed on a surface of the balloon 18', as illustrated in FIG. 3B, or within the matrix 21, as illustrated in FIG. 3C. The balloon 18' may be inelastic or preferably elastic, and is preferably made of polyurethane, Pebax, or other medical grade elastomeric material suitable for constructing puncture-resistant elastic balloons. Balloon 18' is generally inflatable via the balloon luer fitting 26. The rate controlling material may be composed of degradable, partially degradable, nondegradable polymer, synthetic, or natural material. The matrix may degrade by bulk degradation, in which the matrix degrades throughout, or preferably by surface degradation, in which a surface of the matrix degrades over time while maintaining bulk integrity, to allow release of the agent. Alternatively, a nondegradable matrix may release the agent by diffusion through the matrix. Optionally, the rate controlling material may be porous so as to allow elution of the agent from pores. Typically, the agent 19 and/or the matrix 21 are coated, sprayed, dipped, deposited, or painted on the balloon surface.

Figure 4:
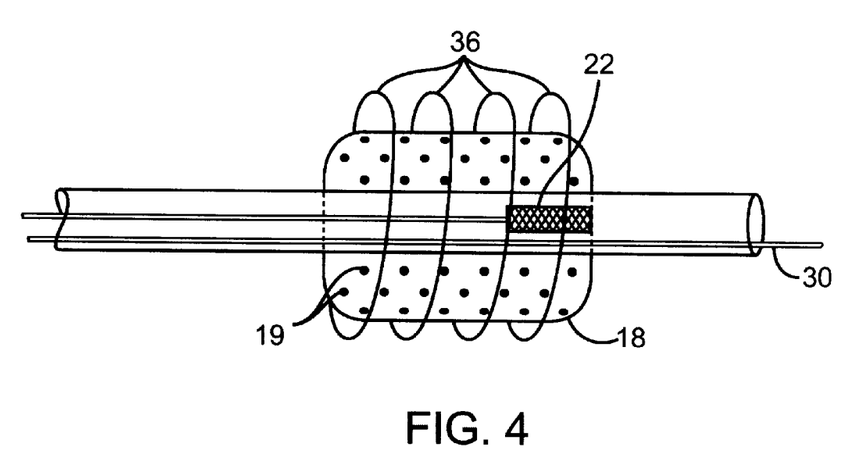
FIG. 4 illustrates a distal tip of the catheter of FIG. 1 with a spiral perfusion balloon.

Referring now to FIG. 4, in some instances, any of the above described balloons may further incorporate a perfusion threading or band 36 affixed to an outer surface of the balloon 18 by adhesion bonding, heat welding, fasteners, or the like. Threading patterns may be spiral (as shown in FIG. 4), helical, or angled. The threading 36 may be formed from polymer materials and may aid in perfusion so as to permit blood flow past the balloon when inflated.

In operation, an appropriately sized catheter 10 according to the present invention is advanced via a guidewire 30 within a blood vessel segment 32 having a treatment region 34 so that the x-ray tube 22 (which is positionable within the balloon 18) and the at least one balloon 18 are positioned at the target region 32. The treatment region 34 has previously been enlarged by balloon angioplasty or other procedures such that atherosclerotic plaque has been radially compressed by expansion of the balloon portion of an angioplasty device (not shown). The balloon 18 (as shown in FIG. 2) is inflated in the blood vessel via the balloon luer fitting 26 and the x-ray tube 22 is turned on and energized. The anti-hyperplasia agent 19 is then released to the target region 34 by any of the means described above while the x-ray tube 22 is translated along an axial line through a center of the balloon 18 to direct an x-ray radiation dose to the target region 34. The combination x-ray radiation and agent delivery is carried out for a predetermined period of time calculated to deliver an effective dosage/concentration to the wall of the blood vessel to inhibit hyperplasia. Moreover, x-ray radiation and agent delivery may be carried out simultaneously or sequentially.

Figure 5:
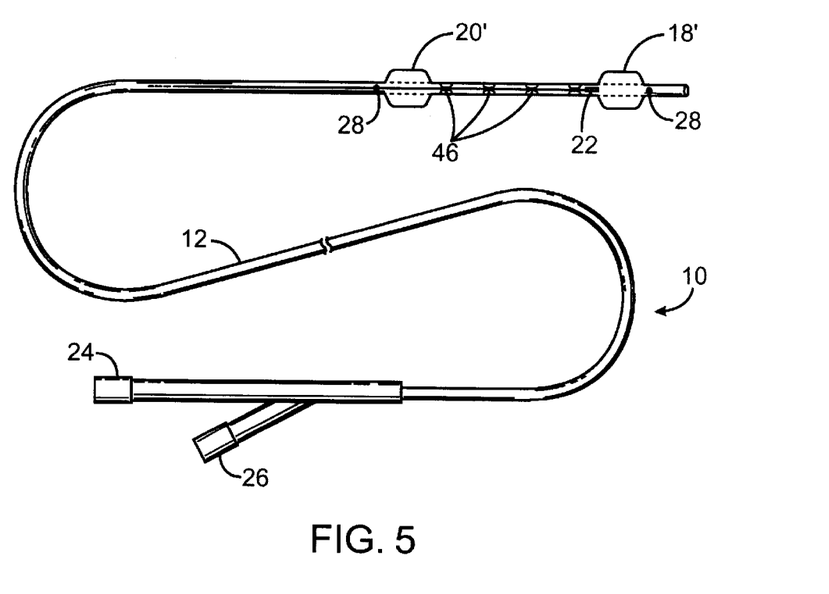
FIG. 5 is a plan view of an alternate embodiment of an apparatus according to the present invention.
Figure 6:
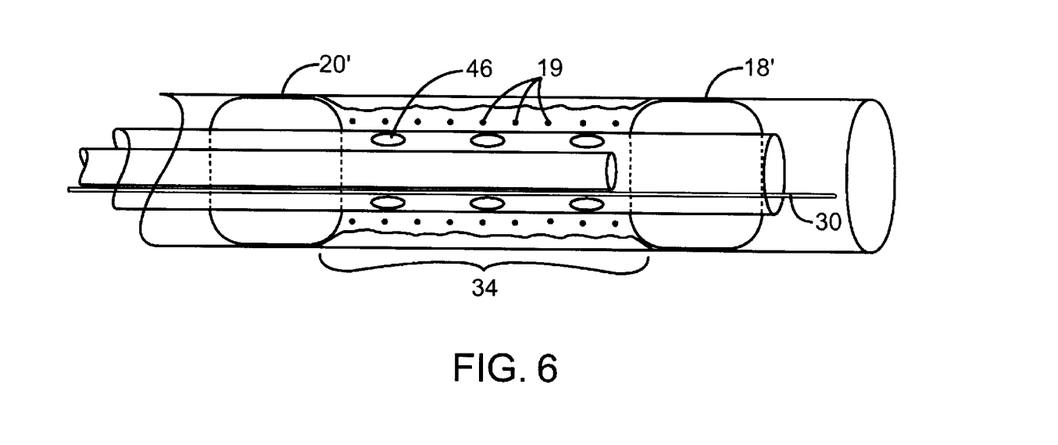
FIG. 6 is a cross sectional view of the apparatus of FIG. 5 within a blood vessel.

Referring now to FIGS. 5 and 6, an alternative embodiment of an apparatus according to the present invention is illustrated. The combined radiation and agent delivery catheter 10 for inhibiting hyperplasia comprises a catheter body 12 having an infusion port 46, a pair of axially spaced apart balloons 18' and 20' on the catheter body 12, and an x-ray tube 22. The infusion ports 46 are in fluid communication with the guidewire lumen. The x-ray tube 22 applies a radiation dose between the axially spaced apart balloons 18' and 20' while the infusion ports 46 directly infuse the agent 19 therein, as shown in FIG. 6.

Balloons 18' and 20' comprise inelastic or preferably elastic balloons, which are preferably made of polyurethane, Pebax, or other medical grade elastomeric material suitable for constructing puncture-resistant elastic balloons. Balloons 18' and 20' are generally inflatable with a commonly used non-toxic radiopaque contrast medium. Suitable inflation media includes Hexabrix 320™ (sold commercially by Mallinkrodt Corp.) and Iopamiron™ (sold commercially by Schering-Plough Corp.). Contrast media with higher concentrations of the radiopaque material (e.g. iodine) are preferred. It is presently preferred that such a two balloon catheter embodiment be employed in the peripheral arteries as such a structure may help center and correctly position the x-ray source 22 in the peripheral vessels, provide a pocket for drug delivery by the infusion ports 46, and aid in uniform radiation dosimetry (which is described in more detail in co-pending U.S. patent application Ser. No. 9/653,444).

In operation, after intravascular intervention, the catheter 10 of FIG. 5 is advanced within the patient's blood vessel 32 by conventional means so that the balloons 18' and 20' are each positioned on an end of a treatment region 34 to isolate the target region. Balloons 18' and 20' are then inflated (via the balloon luer fitting 26) in the blood vessel with non-toxic radiopaque contrast medium until the blood flow past the balloons is substantially stopped (the flow of blood in the vessel itself continues through the perfusion ports 28). Balloons 18' and 20' may also aid in centering the x-ray source 22 within the blood vessel lumen as well as act as markers for proper positioning of the distal end 16 of catheter 10 within the treatment region 34 of the blood vessel under fluoroscopy.

Figure 7:
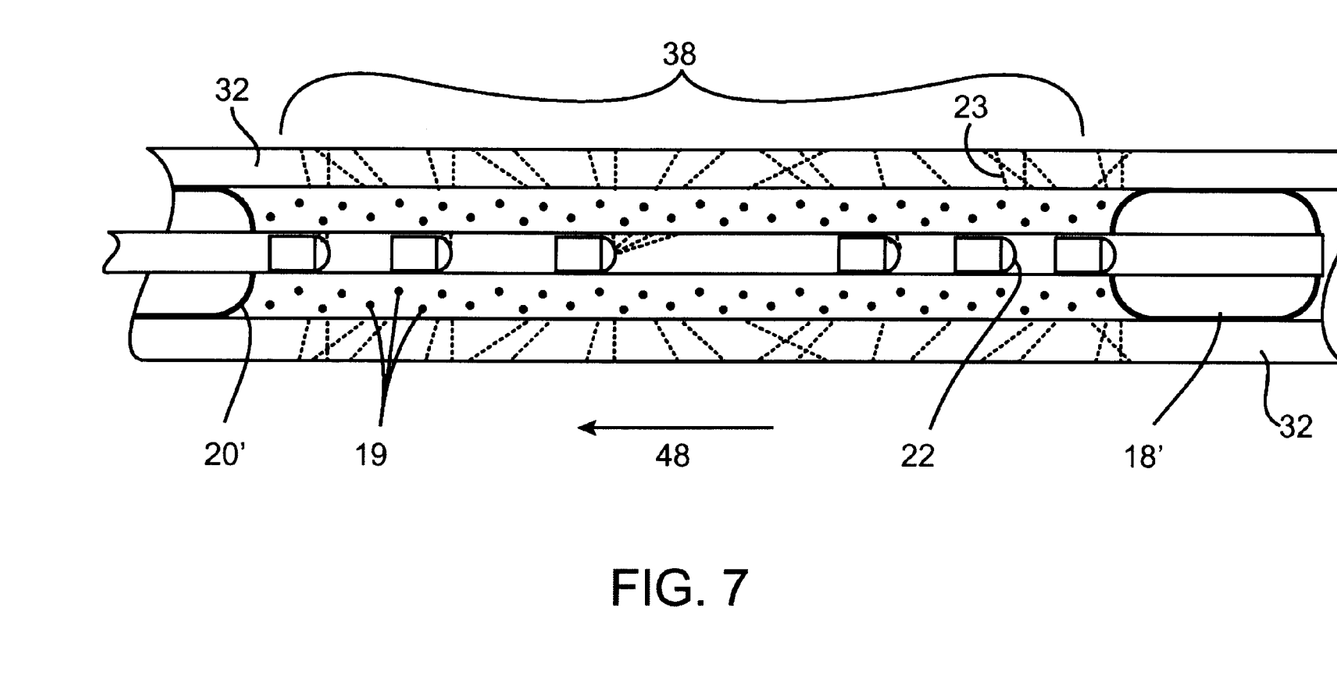
FIG. 7 is a cross sectional view of a translating x-ray source according to an apparatus as modeled in FIG. 5.

Referring now to FIG. 7, the x-ray tube 22 is positioned within the isolated target region, turned on, and translated axially relative to the catheter shaft 12 so that the x-ray tube 22 can travel between balloons 18' and 20' to apply a substantially uniform radiation dose 23 in the radial direction over an entire distance between the axially spaced apart balloons to traverse the target region. The direction of the x-ray source translation is depicted by arrow 48. The agent 19 is also released into the isolated region defined by the first and second balloons 18' and 20' by the infusion ports 46. Balloons 18' and 20' advantageously attenuate radiation from reaching tissue beyond the balloons so as to deliver an effective uniform dose of radiation to the wall of the blood vessel while providing an isolated region or pocket 38 for drug 19 delivery. The combination x-ray radiation and agent delivery is carried out for a predetermined period of time calculated to deliver an effective dosage/concentration to the wall of the blood vessel to inhibit hyperplasia. Moreover, x-ray radiation and agent delivery may be carried out simultaneously or sequentially.

Figure 8:
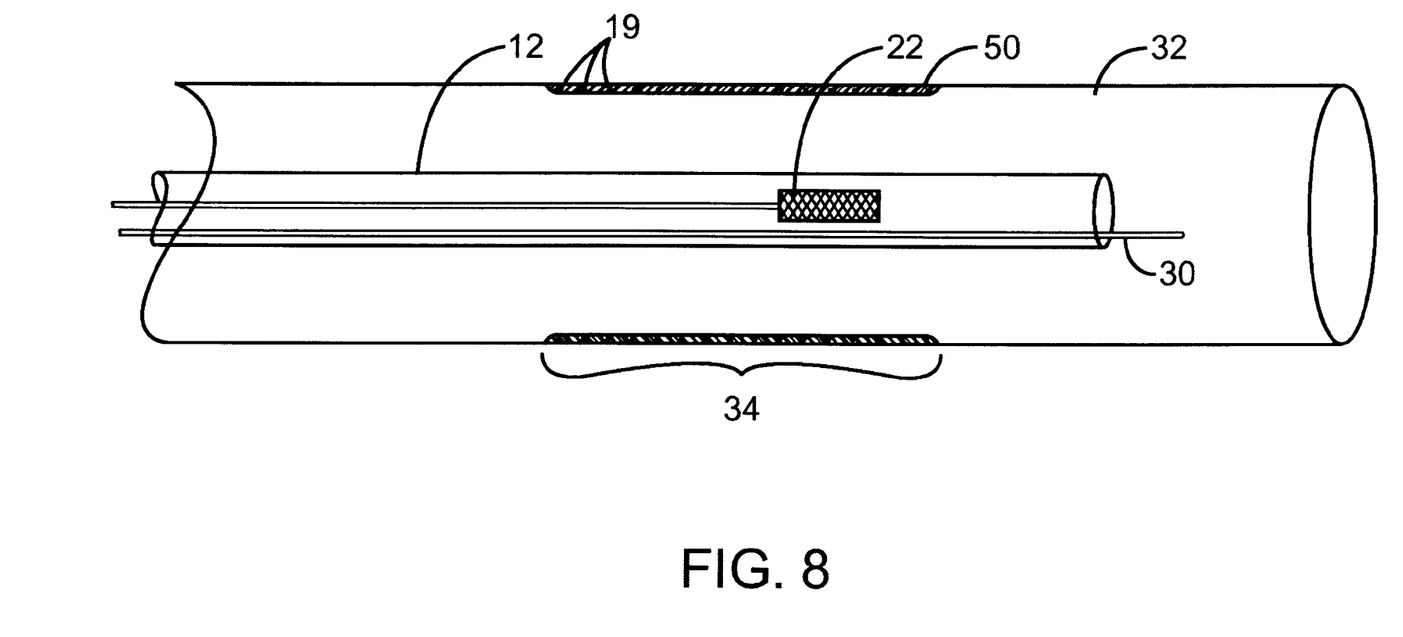
FIG. 8 is a cross sectional view of another alternate embodiment of an apparatus according to the present invention.

Referring now to FIG. 8, an additional embodiment of an apparatus according to the present invention is illustrated. The combined radiation and agent device for inhibiting hyperplasia comprises a catheter body 12, an x-ray tube 22 coupleable to the catheter body 12, a stent 50 releasable from the catheter body 12, and a source of an agent 19 on the stent. The x-ray tube 22 may be positioned within the catheter body 12 to deliver a radiation dose to a vascular region where the stent 50 has been released while the stent 50 releases an agent 19 after it has been implanted in the body lumen 32. The stent 50 may release the agent in a variety of conventional forms. For example, the stent may incorporate a rate controlling matrix, membrane, barrier, or coating to provide controlled release of the agent from the matrix. The agent will typically be disposed on or within stent or within the matrix. Alternatively, the stent may incorporate a porous material which contains the agent, wherein the agent may elute out at a controlled rate from the porous material. Still further, the stent may incorporate a reservoir containing the agent and a cover over the reservoir. Typically, the cover comprises a matrix, membrane, or barrier which in turn controls the rate at which the agent is released from the reservoir.

Figure 9:
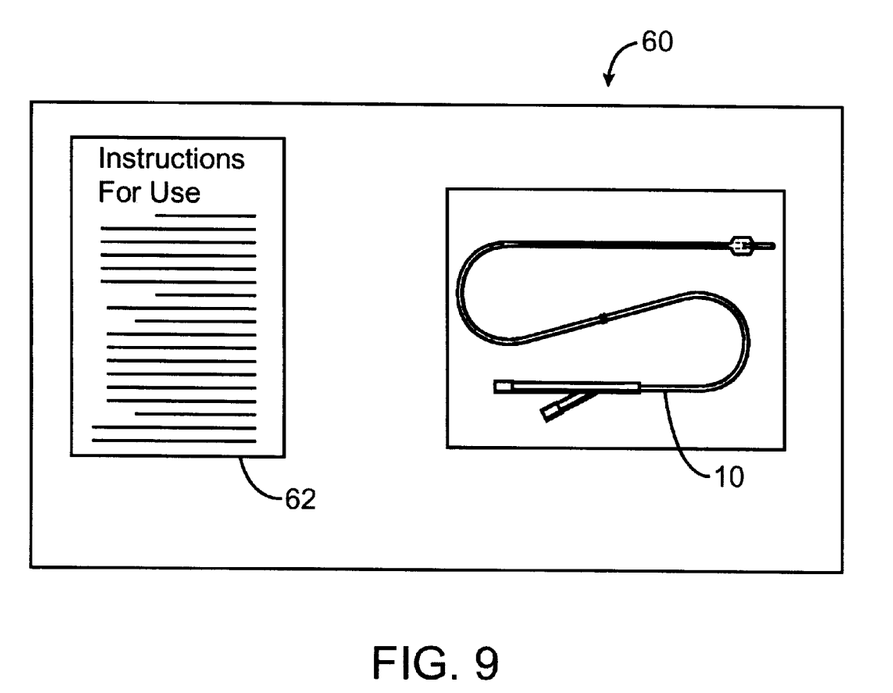
FIG. 9 illustrates a combination radiation and agent delivery kit including the apparatus of FIG. 1 and instructions for its use.

Referring now to FIG. 9, this schematic illustrates a kit 60 including a combination x-ray radiation and agent delivery catheter 10 of FIG. 1 and its instructions for use 62. The combination delivery catheter 10 may be replaced by any of the catheter structures described herein, while the instructions for use 62 will generally recite the steps for aperforming one or more of the above described methods. The instructions 62 will often be printed, optionally being at least in-part disposed on packaging. The instructions 62 may alternatively comprise a videotape, a CD-ROM or other machine readable code, a graphical representation, or the like showing any of the above described methods.

In general, it will be possible to combine the elements of the differing catheters and treatment methods described above. For example, the catheter of FIG. 1 may comprise two microporous balloons, one matrix coated balloon, or a reservoir on the catheter body for releasing the agent. Additionally, the delivery catheter and methods of the present invention may be part of a catheter that combines balloon angioplasty and/or other interventional treatments with the presently claimed radiation and agent delivery catheter.

Although certain preferred embodiments and methods have been disclosed herein, it will be apparent from the foregoing disclosure to those skilled in the art that variations and modifications of such embodiments and methods may be made without departing from the true spirit and scope of the invention. Therefore, the above description should not be taken as limiting the scope of the invention which is defined by the appended claims.

What is claimed is:

1. A combined radiation and agent delivery catheter for inhibiting hyperplasia, comprising:
   a catheter body having a proximal end and a distal end;
   an x-ray tube coupleable to the catheter body for applying a radiation dose to a body lumen;
   a balloon on the catheter body; and
   a matrix formed over at least a portion of the balloon for releasing an agent to the body lumen, wherein the agent is in or beneath the matrix, wherein the combined x-ray tube and matrix for releasing the agent inhibit hyperplasia.

2. A combined radiation and agent delivery catheter for inhibiting hyperplasia, comprising:
   a catheter body having a proximal end and a distal end;
   an x-ray tube coupleable to the catheter body for applying a radiation dose to a body lumen;
   a microporous balloon on the catheter body for releasing an agent to the body lumen, wherein the combined x-ray tube and microporous balloon for releasing the agent inhibit hyperplasia.

3. A delivery catheter as in claim 1 or 2, wherein the agent is selected from the group consisting of radiosensitizer, immunomodulator, cytotoxic agent, cytostatic agent, anti-restenotic agent, and anti-inflammatory agent.

4. A delivery catheter as in claim 1 or 2, wherein the agent is a radiosensitizer selected from the group consisting of taxol, misonidazole, metronidazole, etanidazole, 5-fluorouracil, texaphyrin, C225, and cyclooxygenase-2 inhibitor.

5. A delivery catheter as in claim 1 or 2, wherein the agent is an immunomodulator selected from the group consisting of rapamycin, beta interferon, alpha interferon, methotraxate, cyclosporine, six-mercaptopurine, and cimetidine.

6. A delivery catheter as in claim 1 or 2, wherein the agent comprises taxol incorporated in a solution with polyoxyethylated castor oil and dehydrated alcohol.

7. A delivery catheter as in claim 1 or 2, wherein the agent is attached or encapsulated in a lipid or surfactant carrier.

8. A delivery catheter as in claim 1, wherein the matrix comprises a rate controlling material, wherein the rate controlling material controls the rate at which the agent is released from or through the matrix.

9. A delivery catheter as in claim 8, wherein the agent is released from the matrix by diffusion through the matrix.

10. A delivery catheter as in claim 8, wherein the agent is released from the matrix by degradation of the matrix.

11. A delivery catheter as in claim 8, wherein the rate controlling material is porous and the agent is released from the material by elution from pores.

12. A delivery catheter as in claim 1, wherein the agent is disposed on the balloon.

13. A delivery catheter as in claim 1 or 2, wherein the x-ray tube is positionable within the balloon.

14. A delivery catheter as in claim 1 or 2, wherein the x-ray tube is translatable along an axial direction through a center of the balloon.

15. A delivery catheter as in claim 1 or 2, further comprising perfusion threading on an outer surface of the balloon.

16. A delivery catheter as in claim 15, wherein the threading has a spiral, helical, or angled pattern.

17. A delivery catheter as in claim 1 or 2, wherein the catheter body has a perfusion lumen.

18. A delivery catheter as in claim 2, wherein the microporous balloon contains the agent and the agent is released from the microporous balloon by elution from pores.

19. A delivery catheter as in claim 18, wherein the microporous balloon is inflatable with the agent.

20. A combined radiation and agent delivery catheter for inhibiting hyperplasia, comprising:
    a catheter body having a proximal end, a distal end, and an infusion lumen for releasing an agent;
    a pair of axially spaced apart radiation shielding balloons on the catheter body so as to aid in uniform radiation dosimetry; and
    an x-ray tube coupleable to the catheter body for applying a radiation dose between the axially spaced apart balloons, wherein the combined x-ray tube and infusion lumen for releasing the agent inhibit hyperplasia.

21. A delivery catheter as in claim 20, further comprising a source for releasing at least one agent selected from the group consisting of radiosensitizer, immunomodulator, cytotoxic agent, cytostatic agent, anti-restenotic agent, and anti-inflammatory agent through the infusion lumen.

22. A delivery catheter as in claim 20, further comprising a source for releasing at least one radiosensitizer selected from the group consisting of taxol, misonidazole, metronidazole, etanidazole, 5-fluorouracil, texaphyrin, C225, and cyclooxygenase-2 inhibitor through the infusion lumen.

23. A delivery catheter as in claim 20, further comprising a source for releasing at least one immunomodulator selected from the group consisting of rapamycin, beta interferon, alpha interferon, methotraxate, cyclosporine, six-mercaptopurine, and cimetidine through the infusion lumen.

24. A combined radiation and agent delivery device for inhibiting hyperplasia, comprising:
    a catheter body having a proximal end and a distal end;
    an x-ray tube coupleable to the catheter body for applying a radiation dose to a body lumen;
    a stent releasable from the catheter body, wherein the x-ray tube may be positioned within the catheter body to deliver radiation to a vascular region where the stent has been released; and
    a source of an agent on the stent, wherein the agent is released from the stent after the stent has been implanted in the body lumen.

25. A method for inhibiting hyperplasia in a body lumen, said method comprising:
    releasing an anti-hyperplasia agent at a target region within the body lumen; and
    directing x-ray radiation at the target region, wherein the agent and the x-ray radiation combine to inhibit hyperplasia.

26. A method as in claim 25, further comprising inflating a balloon at the target region, wherein the agent is released from the balloon.

27. A method as in claim 26, wherein the balloon is inflated with the agent and the agent is released from an interior of the balloon through pores.

28. A method as in claim 26, wherein the agent is released from a surface of the balloon.

29. A method as in claim 28, wherein the agent is released through a rate controlling matrix.

30. A method as in claim 26, wherein the directing comprises positioning an x-ray tube within the balloon.

31. A method as in claim 25, further comprising isolating the target region, wherein the agent is released into the isolated region.

32. A method as in claim 31, wherein isolating comprises inflating a pair of axially spaced apart balloons.

33. A method as in claim 31, wherein isolating comprises expanding a pair of axially spaced apart mechanical barriers.

34. A method as in claim 31, wherein directing comprises positioning an x-ray tube within the isolated target region.

35. A method as in claim 30 or 34, wherein positioning comprises energizing the x-ray tube and translating the x-ray tube to traverse the target region.

36. A method as in claim 25, wherein the body lumen is a blood vessel and the target region is a region at risk of hyperplasia.

37. A method as in claim 25, wherein the directing comprises applying a total radiation dose in a range from about 4 Gy to 24 Gy.

38. A method as in claim 25, wherein the releasing the agent and directing an x-ray radiation dose are carried out simultaneously.

39. A method as in claim 25, wherein the releasing the agent and directing an x-ray radiation dose are carried out sequentially.

40. A method for inhibiting hyperplasia in a body lumen, said method comprising:
    positioning an x-ray tube at a target region in the body lumen;

positioning a stent at the target region in the body lumen;
applying an x-ray radiation dose to the target region; and
releasing an agent from the stent to the target region.

41. A kit comprising:
a catheter capable of applying a radiation dose and releasing an agent in a body lumen; and
instructions to use the catheter according to any one of claims 25–40.

42. A kit as in claim 41, further comprising a source of agent.

* * * * *